United States Patent
Maimo et al.

(10) Patent No.: US 6,603,009 B2
(45) Date of Patent: Aug. 5, 2003

(54) METHOD FOR OXIDIZING A THIOETHER GROUP INTO A SULFOXIDE GROUP

(75) Inventors: Ramon Berenguer Maimo, Barcelona (ES); Julio Campon Pardo, Barcelona (ES); Laura Coppi, Barcelona (ES)

(73) Assignee: Esteve Quimica, S.A. (ES)

( * ) Notice: Subject to any disclaimer, the term of this patent is extended or adjusted under 35 U.S.C. 154(b) by 0 days.

(21) Appl. No.: 10/204,506

(22) PCT Filed: Mar. 8, 2001

(86) PCT No.: PCT/ES01/00088
§ 371 (c)(1),
(2), (4) Date: Aug. 20, 2002

(87) PCT Pub. No.: WO01/68594
PCT Pub. Date: Sep. 20, 2001

(65) Prior Publication Data
US 2003/0028030 A1 Feb. 6, 2003

(30) Foreign Application Priority Data
Mar. 13, 2000 (ES) ............................................ 200000595

(51) Int. Cl.[7] .................. A61K 31/4439; C07D 401/12
(52) U.S. Cl. ..................................... 546/273.4; 514/341
(58) Field of Search ....................... 546/273.4; 514/340, 514/341

(56) References Cited

FOREIGN PATENT DOCUMENTS

| CA | 2254597 |   | 6/1999 |   |
|----|---------|---|--------|---|
| EP | 0997461 |   | 5/2000 |   |
| ES | 2026761 |   | 5/1992 |   |
| ES | 2036948 | * | 6/1993 | ............. 546/273.4 |
| ES | 2060541 |   | 11/1994 |   |

OTHER PUBLICATIONS

M. Madesclaire, "Synthesis of Sulfoxides by Oxidation of Thioethers", *Tetrahedron Report No. 210,* 1986, vol. 42, No. 20, pp. 5459–5495.

J. Muzart, "Sodium Perborate and Sodium Percarbonate in Organic Synthesis", *Synthesis,* 1995, vol. 11, pp. 1325–1347.

A. McKillop, et al., "Sodium Perborate and Sodium Percarbonate: Cheap, Safe and Versatile Oxidising Agents for Organic Synthesis", *Tetrahedron,* 1995, vol. 51, No. 22, pp. 6145–6166.

S. Maignien, et al., "A Practical Molybdenum–Catalyzed Oxidation of Alcohols by Sodium Percarbonate", *Synlett,* May 1996, vol. 5, pp. 439–440.

* cited by examiner

*Primary Examiner*—Alan L. Rotman
*Assistant Examiner*—Janet Coppins
(74) *Attorney, Agent, or Firm*—Ostrolenk, Faber, Gerb & Soffen

(57) ABSTRACT

The present invention relates to a procedure for the oxidation of a thioether group to a sulfoxide group, with aqueous sodium percarbonate in the presence of a molybdenum salt as a catalyst. The procedure is of application to oxidize the thioether group of a compound (I), where $R_1$ is a $C_1$–$C_6$ alkyl, a halogenated $C_1$–$C_6$ alkyl, or —$(CH_2)_n$—$OR_9$, where n is an integer between 1 and 6 and $R_9$ is H or a $C_1$–$C_6$ alkyl; $R_2$, $R_3$, $R_4$, $R_5$, $R_6$ and $R_8$, independently form each other represent H, a $C_1$–$C_6$ alkyl, or $C_1$–$C_6$ alkoxy; and $R_7$ is H, a $C_1$–$C_6$ alkyl, a $C_1$–$C_6$ alkoxy or a $C_1$–$C_6$ fluorinated alkoxy, in order to obtain the sulfinyl derivative (II).

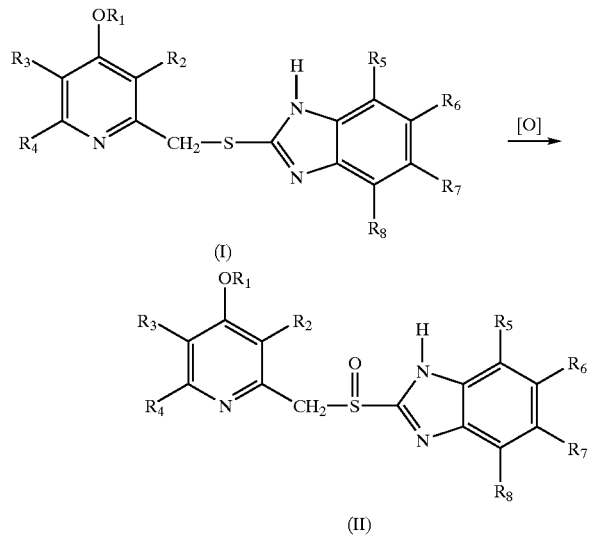

20 Claims, No Drawings

METHOD FOR OXIDIZING A THIOETHER GROUP INTO A SULFOXIDE GROUP

FIELD OF THE INVENTION

The present invention relates to a procedure for oxidation of a thioether group to a sulfoxide group. More specifically, it relates to a procedure for oxidation of a thioether group in a compound with the formula (I) to a sulfoxide group, to obtain the sulfinyl derivative with the formula (II). IN said formulae (I) and (II), $R_2$, $R_3$, $R_4$, $R_5$, $R_6$ and $R_8$, independently from each other represent hydrogen, an alkyl group with 1 to 6 carbon atoms, or an alkoxy group with 1 to 6 carbon atoms; $R_7$ represents hydrogen, an alkyl group with 1 to 6 carbon atoms, an alkoxy group with 1 to 6 carbon atoms or a fluorinated alkoxy group with 1 to 6 carbon atoms; and $R_7$ represents an alkyl group with 1 to 6 carbon atoms, a halogenated alkyl group with 1 to 6 carbon atoms, or a group such as —$(CH_2)_n$—$OR_9$, where n is an integer between 1 and 6, both inclusive, and $R_9$ represents hydrogen or an alkyl group with 1 to 6 carbon atoms.

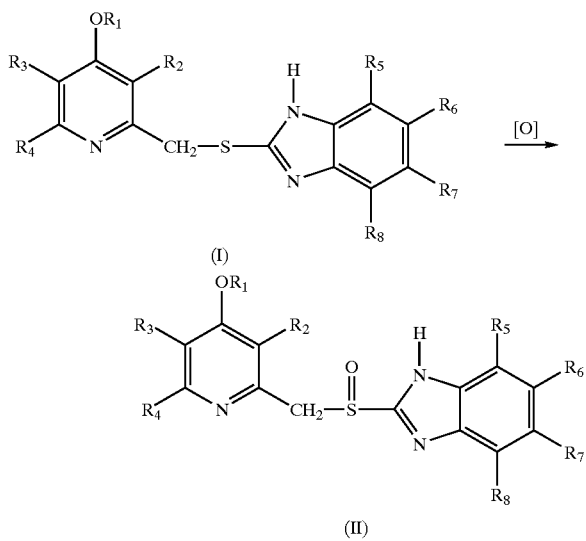

BACKGROUND OF THE INVENTION

The development of procedures for synthesizing compounds with the formula (II), particularly those meant to obtain compounds with an important therapeutic activity, such as lansoprazol, 2-[[[3-methyl-4-(2,2,2-trifluoroethoxy)-2-pyridinyl]methyl]sulfinyl]-1H-benzimidazol, omeprazol, 2-[[(3,5-dimethyl-4-methoxy-2-pyridinyl)methyl]sulfinyl]-5-methoxy-1H-benzimidazol, rabeprazol, 2-[[[3-methyl-4-(3-methoxypropoxy)-2-pyridinyl]methyl]sulfinyl]-1H-benzimidazol, and pantoprazol, 5-difluoromethoxy-2-[[(3,4-dimethoxy-2-pyridinyl)methyl] sulfinyl]-1H-benzimidazol, which are known as agents which inhibit gastric secretions and are administered to mammals for treating gastrointestinal ailments such as gastritis, gastric and duodenal ulcers, has been the object of many patents, without solving certain serious drawbacks related to these procedures.

In this sense are known in the state of the art several synthesis procedures for these 2-(2-pyridinylmethylsulfinyl) benzimidazols with the formula (II) which basically involve the synthesis of the precursor thioether and its subsequent oxidation to a sulfinyl group. Several procedures have been described for the synthesis of lansoprazol and related products such as that in patent EP-174726, which describes a procedure for oxidation of sulfur with one of m-chloroperbenzoic, peracetic, trifluoroperacetic or permalic acids, sodium bromite or sodium hypochlorite, or hydrogen peroxide.

Patent application WO98/09962 describes a method for preparing omeprazol by oxidation of its thioether precursor with a peroxyacetic acid in a biphasic medium of water and a chlorinated organic solvent. Likewise, patent application WO99/25711 also describes a method for the separation of omeprazol in which the oxidation of the thioether precursor is realized with cumenum hydroperoxide or t-butyl hydroperoxide in the presence of a titanium complex.

EP-302720 describes a procedure in which oxidation of the thioether group of compounds as 2-(2-pyridinylmethylthio) benzimidazols is achieved with hydrogen peroxide, using as catalyst vanadium pentoxide, sodium metavanadate, ammonium metavanadate or vanadium (IV) acetylacetonate.

WO98/40378 describes a procedure in which the oxidation of the thioether group of compounds as 2-(2-pyridinylmethylthio) benzimidazols is achieved by compounds of the peroxy type, such as peracids, alkylhydroperoxides, benzoylperoxides, hydrogen peroxide, metaperiodates and tetraalkylammonium perborates, etc., and as catalyst are used vanadium compounds.

Patent application WO99/02521 describes a method for oxidation of thioether to sukphoxide based on the use of a peroxoborate salt in the presence of an anhydride acid or a metal catalyst, or with an N-halosuccinimide, 1,3-dihalo-5,5-dimethylhidantoine or a salt of dichloroisocyanuric acid in the presence of a base.

Patent ES-2105953 describes the conditions for oxidation of thioether to sulfoxide based on the use of hydrogen peroxide in a medium of sodium bicarbonate, catalyzed by phosphotungstenic acid $H_3(P(W_3O_{10})_4)xH_2O$.

Patent ES-2060541 describes a procedure for oxidation of sulfur to sulfoxide with potassium peroxymonosulfate, with or without the presence of a ketone, or with hydrogen peroxide, in the presence of catalysts of Mo and V acetylacetonate.

Another patent which describes the oxidation of sulfur to sulfoxide with t-butyl hydroperoxide catalyzed by vanadium is ES-2063705, in this case for the synthesis of lansoprazol.

U.S. Pat. No. 5,374,730 describes an oxidation stage of sulfur to sulfoxide with hydrogen peroxide and catalyzed by vanadium acetylacetonate.

Patent ES-2036948 describes a procedure for the synthesis of lansoprazol, in which the last stage involves the oxidation of the thioether precursor of lansoprazol to sulfoxide, with m-chloroperbenzoic acid or magnesium monoperoxyphthalate in the presence of a quaternary ammonium salt, or hydrogen peroxide, with a W or molybdenum catalyst.

From the state of the art it is inferred that the procedure which has been developed farthest and is more widely used for oxidation is that which employs vanadium catalysts. Among these basic procedures the most efficient is the one which uses hydrogen peroxide and vanadium catalyst; and the one which uses magnesium monoperoxyphthalate (MMPP), as described in patent EP-533264. Despite this, there are unsolved drawbacks in these procedures such as the fact that vanadium compounds are relatively toxic, and that MMPP is expensive to use industrially, as well as generating phthalic acid as a reaction byproduct. Finally, in both cases sulfone and N-oxide are produced as impurities due to overoxidation. Production of these impurities obviously results in increased costs in the procedures for obtaining any of these products.

The procedure described for oxidation of the thioether precursor of lansoprazol involving the use of hydrogen peroxide and molybdenum catalysts also does not give good results as it has the drawback of producing a large amount of sulfone and some N-oxide as undesirable byproducts.

The need therefore exists to develop an improved procedure for the oxidation of these thioethers to sulfoxide, and in particular applicable to synthesis of omeprazol, lansoprazol, rabeprazol and pantoprazol, or their precursors.

DETAILED DECRIPTION OF THE INVENTION

The present invention relates to a procedure for oxidation of a thioether group to a sulfoxide group, and in particular for oxidation of a thioether group of a compound with the formula (I) as defined above, to a sulfinyl derivative with the formula (II).

In the sense used in this description, the term "halogenated alkyl group with 1 to 6 carbon atoms" signifies an alkyl group with 1 to 6 carbon atoms which contains one or more halogen atoms, preferably fluorine or chlorine, substituting one or more hydrogen atoms. Similarly, the term "fluorinated alkoxy group with 1 to 6 carbon atoms" signifies an alkoxy group with 1 to 6 carbon atoms which contains one or more fluorine atoms substituting one or more hydrogen atoms, such as 2,2,2-trifluoroethoxy or difluoromethoxy.

The procedure involves the oxidation of the thioether with sodium percarbonate in the presence of a molybdenum salt as a catalyst, which is preferably ammonium molybdate. This new procedure has proved to be more efficient than the various procedures described in the discussion on the state of the art. Additionally, sodium percarbonate stands out as an oxidizing agent which is easy to handle, relatively stable and simple to store.

The procedure of the present invention presents a number of improvements on the previous procedures, such as the following:

the reagents used are commercially affordable,
molybdenum catalysts are less toxic than vanadium catalysts,
the pH of the reaction mixture is slightly basic and thus adequate for stability of compounds such as lansoprazol in a solution,
the formation of N-oxide as an impurity is unappreciable or appreciable at negligible amounts,
the percentage of sulfone produced is low,
the oxidized product can be isolated by precipitation in the reaction medium,
a first purification of the sample can be performed by a fractionated precipitation at a controlled pH.

In addition, the oxidation was attempted with vanadium catalysts, but the results obtained were not satisfactory.

In a preferred realization of the procedure of the invention the oxidation is effected with a molar ratio of sodium percarbonate to the thioether with the formula (I) ranging between 0.5 and 1.4, and preferably between 0.6 and 1.2.

The amount of catalyst (molybdenum salt) employed is between 0.3% and 7%, and preferably between 0.5% and 5%, by weight, with respect to the thioether with formula (I).

The solvent used for the oxidation reaction is an alcohol with a low molecular mass, preferably methanol.

The reaction temperature is between −10° C. and 25° C., preferably between −5° C. and 20° C.

Among the compounds with the formula (II) are lansoprazol, omeprazol, rabeprazol, pantoprazol and 2-[[[4-(3-hydroxypropoxy)-3-methyl-2-pyridinyl]methyl] sulfinyl]-1H-benzimidazol, which may be obtained from the corresponding thioether precursors by oxidation of the thioether group to a sulfoxide group according to the procedure provided by this invention. In a particular realization, said compounds with formula (II) are obtained by oxidation of the thioether group present in the thioether precursors with the corresponding formula (I) to sulfoxide, in methanol (solvent) with sodium percarbonate in a molar ratio with respect to the initial thioether ranging between 0.6 and 1.2, in the presence of ammonium molybdate (catalyst) with a ratio of ammonium molybdate with respect to the initial thioether between 0.5% and 5% by weight, and at a temperature between −5° C. and 20° C.

2-[[[4-(3-hydroxypropoxy)-3-methyl-2-pyridinyl] methyl]sulfinyl]-1H-benzimidazol may be used as a material for the synthesis of rabeprazol by the transformation of the hydroxyl group into a methoxy group.

The following examples are provided for purposes of illustration only and should not be understood as a definition of the limits of the invention.

EXAMPLE 1

Preparation of Lansoprazol 10 g of 2-[[[3-methyl-4-(2,2,2-trifluoroethoxy)-2-pyridinyl]methyl]thio]-1H-benzimidazol were dissolved in 50 ml of methanol and 0.3 g of ammonium molybdate were added. The solution was cooled to 10° C., and 3.35 g of sodium percarbonate added slowly, kept stirred at the same temperature for 15 hours. After the reaction ended 250 ml of water were added and the pH of the resulting mixture adjusted to 10 with 10% acetic acid. This was kept stirred for 1 hour and the solid obtained was filtered, and subsequently washed with water and dried in a vacuum oven at 40° C. This provided 9.4 g of lansoprazol (yield: 90%).

EXAMPLE 2

Preparation of Omeprazol 30 g of 2-[[(3,5-dimethyl-4-methoxy-2-pyridinyl)methyl] sulfinyl]-5-methoxy-1H-benzimidazol were dissolved in 150 ml of methanol and 0.9 g of ammonium molybdate were added. The solution was cooled to 10° C. and 11.7 g of sodium percarbonate were added slowly and kept at this temperature for 15 hours, after which 450 ml of water were added slowly and the pH adjusted to 8.6 with 10% acetic acid. The resulting solid was filtered and then washed with water and acetone. After drying in a vacuum oven at 30/35° C., 25.4 g of omeprazol were obtained (yield: 81%).

EXAMPLE 3

Preparation of Rabeprazol 2.3 g of 2-[[[3-methyl-4-(3-methoxypropoxy)-2-pyridinyl]methyl]thio]-1H-benzimidazol were dissolved in 11.5 ml of methanol and 90 mg of ammonium molybdate were added. The solution was cooled to 5° C. and 0.87 g of sodium percarbonate were added, then kept stirred at this temperature for 6 h. After the reaction finished 22 ml of water were added, then heating to 20° C. and adjusting the pH of the mixture to 7.5 with acetic acid. The mixture is extracted with 50 ml of dichloromethane and the organic phase was separated, which was then washed with 100 ml of water. The solvent was evaporated at a reduced pressure. 2.0 g of rabeprazol were obtained (yield: 81%).

EXAMPLE 4

Preparation of Pantoprazol 310 mg of 5-difluoromethoxy-2-[[(3,4-dimethoxy-2-pyridinyl)methyl]thio]-1H-benzimidazol were dissolved in 1.5 ml of methanol and 12 mg of ammonium molybdate added. The solution was cooled to 51C and 0.11 g of sodium percarbonate were added, then kept stirred at the same temperature for 4 h. After the reaction ended 3 ml of water were added, then heating to 20° C. and adjusting the mixture of the pH to 7.5 with acetic acid. The mixture is extracted with 5 ml of dichloromethane and the organic phase separated, then washed with 10 ml of water. The solvent was evaporated at a reduced pressure. 274 mg of pantoprazol were obtained (yield: 88%).

EXAMPLE 5

Preparation of 2-[[[3-methyl-4-(3-hidroxypropoxy)-2-pyridinyl]methyl]sulfinyl]-1H-benzimidazol 2.2 g of 2-[[[4-(3-hidroxypropoxy)-3-methyl-2-pyridinyl]methyl]thio]-1H-benzimidazol were dissolved in 11.5 ml of methanol and 90 mg of ammonium molybdate were added. The solution was cooled to 5° C. and 0.87 g of sodium percarbonate were added, then stirring at the same temperature for 6 h. After the reaction ended 22 ml of water were added, then heating to 20° C. and adjusting the pH of the mixture to 7.5 with acetic acid. The mixture was extracted with 150 ml of dichloromethane and the organic phase separated. The solvent was evaporated at reduced pressure, providing 2.0 g of 2-[[[4-(3-hydroxypropoxy)-3-methyl-2-pyridinyl]methyl]sulfinyl]-1H-benzimidazol (yield: 86%).

What is claimed is:

1. A process for oxidizing a 2-(2-pyridinylmethyl-thio) benzimidazol compound of formula I to a compound of formula II, comprising carrying out said oxidation in the presence of sodium percarbonate and a molybdenum salt catalyst according to the following reaction:

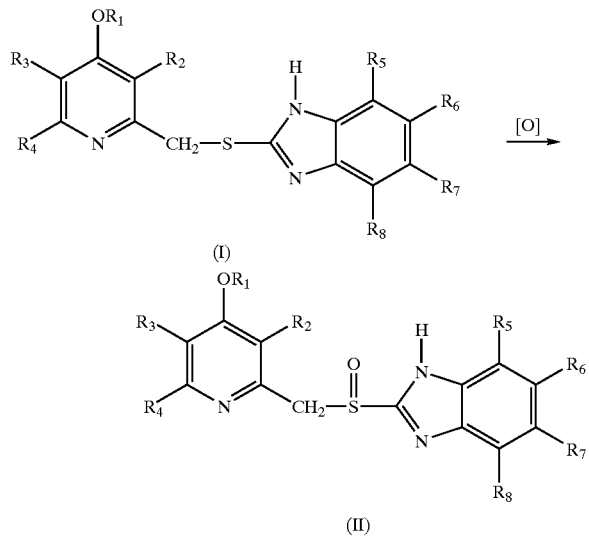

wherein $R_1$ is selected from the group consisting of an alkyl group with 1 to 6 carbon atoms, a halogenated alkyl group with 1 to 6 carbon atoms, and a $-(CH_2)_n-OR_9$ group, wherein n is an integer from 1 to 6, and $R_9$ represents hydrogen or an alkyl group with 1 to 6 carbon atoms;

$R_2$, $R_3$, $R_4$, $R_5$, $R_6$ and $R_8$, independently from each other are selected from the group consisting of hydrogen, an alkyl group with 1 to 6 carbon atoms, and an alkoxy group with 1 to 6 carbon atoms; and $R_7$ is selected from the group consisting of hydrogen, an alkyl group with 1 to 6 carbon atoms, an alkoxy group with 1 to 6 carbon atoms, and a fluorinated alkoxy group with 1 to 6 carbon atoms.

2. The process of claim 1, wherein the molybdenum salt is ammonium molybdate.

3. The process of claim 1, wherein the ratio of the molybdenum salt with respect to the thioether is between 0.3% and 7% by weight.

4. The process of claim 3, wherein the ratio of the molybdenum salt is between 0.5% and 5% by weight with respect to the thioether.

5. The process of claim 1, wherein the molar ratio of sodium percarbonate to thioether is between 0.5 and 1.4.

6. The process of claim 5, wherein the molar ratio of sodium percarbonate to thioether is between 0.6 and 1.2.

7. The process of claim 1, wherein said oxidation is carried out at a temperature between −10° C. and 25° C.

8. The process of claim 7, wherein said oxidation is carried out at a temperature between −5° C. and 20° C.

9. The process of claim 1, wherein said oxidation is carried out in an alcohol solvent.

10. The process of claim 9, wherein the alcohol is methanol.

11. A process for synthesizing lansoprazol comprising carrying out the oxidation reaction of the thioether precursor according to claim 1 as a last step of the synthesis.

12. The process of claim 11, wherein the oxidation of the thioether group of 2-[[[3-methyl-4-(2,2,2-trifluoroethoxy)-2-pyridinyl]methyl]thio]-1H-benzimidazol to sulfoxide is carried out in a methanol solvent using sodium percarbonate in a molar ratio with respect to the initial thioether between 0.6 and 1.2, and ammonium molybdate as a catalyst, with a ratio of ammonium molybdate ranging between 0.5% and 5% by weight with respect to the thioether, and at a reaction temperature between −5° C. and 20° C.

13. A process for synthesizing omeprazol comprising carrying out the oxidation reaction of the thioether precursor according to claim 1 as a last step of the synthesis.

14. The process of claim 13, wherein the oxidation of the thioether group of 2-[[3,5-dimethyl-4-methoxy-2-pyridinyl)methyl]sulfinyl]-5-methoxy-1H-benzimidazol to sulfoxide is carried out in a methanol solvent using sodium percarbonate in a molar ratio with respect to the initial thioether between 0.6 and 1.2, and ammonium molybdate as a catalyst, with a ratio of ammonium molybdate ranging between 0.5% and 5% by weight with respect to the thioether, and at a reaction temperature between −5° C. and 20° C.

15. A process for synthesizing rabeprazol comprising carrying out the oxidation reaction of the thioether precursor according to claim 1 as a last step of the synthesis.

16. The process of claim 15, wherein the oxidation of the thioether group of 2-[[[3-methyl-4-(3-methoxypropoxy)-2-pyridinyl]methyl]thio]-1H-benzimidazol to sulfoxide is carried out in a methanol solvent using sodium percarbonate in a molar ratio with respect to the initial thioether between 0.6 and 1.2, and ammonium molybdate as a catalyst, with a ratio of ammonium molybdate ranging between 0.5% and 5% by weight with respect to the thioether, and at a reaction temperature between −5° C. and 20° C.

17. A process for synthesizing pantoprazol comprising carrying out the oxidation reaction of the thioether precursor according to claim 1 as a last step of the synthesis.

18. The process of claim 17, wherein the oxidation of the thioether group of 5-difluoromethoxy-2-[[(3,4-dimethoxy-2-pyridinyl)methyl]thio]-1H-benzimidazol to sulfoxide is carried out in a methanol solvent using sodium percarbonate in a molar ratio with respect to the initial thioether between 0.6 and 1.2, and ammonium molybdate as a catalyst, with a ratio of ammonium molybdate ranging between 0.5% and 5% by weight with respect to the thioether, and at a reaction temperature between −5° C. and 20° C.

19. A process for synthesizing 2-[[[3-methyl-4-(3-hidroxypropoxy)-2-pyridinyl]methyl]sulfinyl]-1H-benzimidazol comprising carrying out the oxidation reaction of the thioether precursor according to claim 1 last step of the synthesis.

20. The process of claim 19, wherein the oxidation of the thioether group of 2-[[[3-methyl-4-(3-hidroxypropoxy)-2-pyridinyl]methyl]thio]-1H-benzimidazol to sulfoxide takes place in methanol as a solvent, using sodium percarbonate in a molar ratio with respect to the initial thioether between 0.6 and 1.2, and ammonium molybdate as a catalyst, with a ratio of ammonium molybdate ranging between 0.5% and 5% by weight with respect to the thioether, and at a reaction temperature between −5° C. and 20° C.

* * * * *

UNITED STATES PATENT AND TRADEMARK OFFICE
CERTIFICATE OF CORRECTION

PATENT NO. : 6,603,009 B2
DATED : August 5, 2003
INVENTOR(S) : Maimo et al.

It is certified that error appears in the above-identified patent and that said Letters Patent is hereby corrected as shown below:

Column 4,
Line 50, please change "sulfinyl" to -- thio --.

Column 6,
Line 51, please change "sulfinyl" to -- thio --.

Signed and Sealed this

Fifteenth Day of February, 2005

JON W. DUDAS
*Director of the United States Patent and Trademark Office*